United States Patent [19]

Vanderkooi et al.

[11] Patent Number: 4,947,850
[45] Date of Patent: Aug. 14, 1990

[54] METHOD AND APPARATUS FOR IMAGING AN INTERNAL BODY PORTION OF A HOST ANIMAL

[75] Inventors: Jane Vanderkooi; David Wilson, both of Philadelphia, Pa.

[73] Assignee: Trustees of the University of Pennsylvania, Philadelphia, Pa.

[21] Appl. No.: 166,710

[22] Filed: Mar. 11, 1988

[51] Int. Cl.$^5$ .............................. A61B 5/00
[52] U.S. Cl. ......................... 128/654; 128/665
[58] Field of Search ........................ 128/633–635, 128/654, 664, 665

[56] References Cited

U.S. PATENT DOCUMENTS

| | | | |
|---|---|---|---|
| 3,285,703 | 11/1966 | Narita et al. | |
| 3,612,866 | 10/1971 | Stevens | 250/71 |
| 3,647,387 | 3/1972 | Benson et al. | 23/232 R |
| 3,654,463 | 4/1972 | Geusic et al. | 250/71 R |
| 4,541,438 | 9/1985 | Parker et al. | 128/664 |
| 4,577,636 | 3/1986 | Spears | 128/654 |
| 4,651,744 | 3/1987 | Bristow et al. | 128/665 X |
| 4,768,513 | 9/1988 | Suzuki | 128/634 |
| 4,773,097 | 9/1988 | Suzuki et al. | 128/665 X |
| 4,810,655 | 3/1989 | Khalil et al. | 128/665 X |

FOREIGN PATENT DOCUMENTS 2132348A  7/1984  United Kingdom.

OTHER PUBLICATIONS

An Optical Method for Measurement of Dioxygen Concentration Based Upon Quenching of Phosphorescence, Jane M. Vanderkooi et al., Journal of Biological Chemistry, vol. 262, No. 12, issue of Apr. 25, pp. 5476–5482, 1987.

A New Method for Measuring Oxygen Concentration of Biological Systems, Jane M. Vanderkooi and David F. Wilson, Oxygen Transport to Tissue VIII, Longmuir, ed., Plenum, (Aug. 1986).

Primary Examiner—Ruth S. Smith
Attorney, Agent, or Firm—Woodcock Washburn Kurtz Mackiewicz & Norris

[57] ABSTRACT

A method and associated apparatus for imaging an oxygen-containing, internal body portion of a host animal which comprises: (a) adding to a body fluid of the host animal a phosphorescent composition (e.g., zinc verdin or a metal porphyrin compound) compatible with said body fluid, the phosphorescence of said composition being quenchable with oxygen in said body portion; (b) irradiating said body portion with a pulse of light at a wavelength and for a time sufficient to effect phosphorescence of said composition to be emitted as light from said body portion; (c) scanning across said body portion to measure the decay of said emitted phosphorescence across said body portion; (d) relating any variations in said decay measured across said body portion to variations in structure of said body portion based on oxygen contained by the body portion; and displaying an image of said body portion.

18 Claims, 1 Drawing Sheet

METHOD AND APPARATUS FOR IMAGING AN INTERNAL BODY PORTION OF A HOST ANIMAL

GOVERNMENT SUPPORT

Portions of this invention were supported by National Institutes of Health grant GM-36393.

BACKGROUND OF THE INVENTION

This invention relates to imaging internal body portions of animals.

Animals, especially mammals, are dependent upon having an adequate oxygen supply in their body tissues. In mammals, the circulatory system employs specialized oxygen-carrying molecules in the blood to deliver oxygen from the lungs to other tissues throughout the body. Thus, every organ in the body contains oxygen in varying amounts and concentrations in every tissue. The distribution of oxygen in tissue can be indicative of structure, anomalies, defects or disease.

It is known that oxygen can have a quenching effect on the molecular luminescence of various aromatic chemical compounds and that this property can be used in the measurement of oxygen concentrations as shown in Stevens, U.S. Pat. No. 3,612,866. Bacon et al, in U.K. patent application No. GB 2,132,348A, published July 4, 1984, disclose inter alia using a fluorescent material to measure levels of oxygen in blood both in vitro and in vivo using a fiber optic probe or catheter.

An optical technique for imaging internal body structures based on the varying oxygen concentration of tissue which is not invasive or otherwise harmful would be very useful. For example, it could be used in examining soft body tissue for anomalies in the vasculature which generally accompany tumor formulation, and for obtaining detailed diagnostic information on many types of vascular defects, e.g., constrictions, varicosities, or aneurisms.

The inventors of this invention have previously disclosed methods for measuring oxygen concentration in biological systems using oxygen-dependent phosphorescent quenching of lumiphores. See Vanderkooi and Wilson, "A New Method for Measuring Oxygen Concentration in Biological Systems" *Oxygen Transport to Tissue VIII*, Longmuir, ed, Plenum (August, 1986). No method of imaging using such techniques has been known heretofore, however.

SUMMARY OF THE INVENTION

This invention provides such a useful, noninvasive technique and enables imaging of internal body structures of animals based on the varying oxygen concentration of tissue as particularly pointed out in the appended claims and described in its preferred embodiments in the following specification.

DETAILED DESCRIPTION OF THE INVENTION

Figure 1:
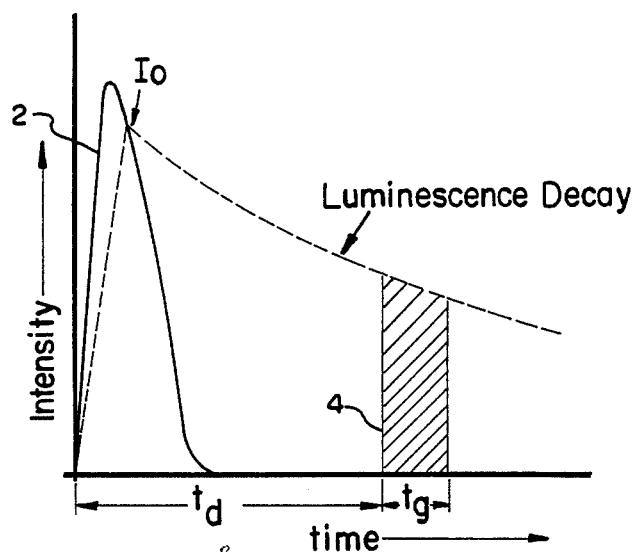
FIG. 1 is a graphical representation of the time and intensity of light flash and phosphorescence decay.

In accordance with the present invention, methods are provided for imaging oxygen-containing internal body portions of host animals. These methods comprise adding to a body fluid of the host animal a phosphorescent composition compatible with the body fluid. The phosphorescent composition is selected to be quenchable with oxygen in the body portion to be imaged. The method further comprises of radiating the body portion with light at a wavelength and for a time sufficient to effect phosphorescence of the composition. The light may be continuous, pulsed or modulated depending on the embodiment of the invention. The phosphorescence is emitted as light from the body portion. The body portion is then scanned to measure the phosphorescence intensity (continuous illumination) or the time dependence of phosphorescence (pulsed or modulated illumination). The phosphorescence intensity or, in the more accurate embodiment, the decay of the emitted phosphorescent light from the body portion and variations in the decay measured across the body portion are then related to variations in structure of the body portion based upon oxygen contained in the body portion.

In accordance with other embodiments of the invention, methods for imaging oxygen-containing internal body portions of mammals are provided. These comprise adding to a circulatory system of the mammal a phosphorescent composition compatible with the circulatory system and quenchable with oxygen. Phosphorescent composition is selected to be differentially absorbable by the body portion to be imaged. The body portion is then irradiated with a pulse of light at a wavelength less than about 700 nanometers for a time sufficient to effect phosphorescence of the composition. This phosphorescence is emitted as light of a wavelength above about 650 to about 1100 nanometers from the body portion. The body portion is then scanned to measure and record the intensity of the emitted phosphorescence at a plurality of times after the radiation. The time dependence of decay of the intensity of emitted phosphorescence is then determined across the body portion. Variations in the decay measured across the body portion is then related to variations in structure of the body portion such as would be produced by deformations, defects, tumors, disease, or other variations, said variations being related to the oxygen contained in the body portion and/or to the phosphorescent composition contained therein. In accordance with still other embodiments, these methods are effected through digitization of the time dependence of decay as determined in the foregoing steps.

In other embodiments to the invention, apparatus for imaging oxygen-containing internal body portions of the host animal which contain body fluid can be attained. The body fluid is caused to contain a phosphorescent composition quenchable with oxygen. The apparatus includes means for radiating the body portion with a pulse of light at a wavelength in the visible or near-infrared region (less than 700 nanometers) for a period of time sufficient to effect phosphorescence of the composition when in the body portion to be imaged. The apparatus further comprises means for scanning across the body portion to measure the intensity of phosphorescent emitted light from the composition in the body portion, preferable at a wavelength greater than about 650 to about 1100 nanometers. Timing means are also provided for regulating the irradiation means and the scanning means. The scans have emitted light only at a determined time and at time intervals after the irradiating pulse. The scanning means is connected to means for measuring decay in the intensity of the emitted phosphorescent light at a plurality of locations across the body portion at said determined time intervals and means to relate any variations in decay of the phosphorescent emission at those locations on the body portion to the structure of said body portion.

In accordance with the invention, the wavelength of incident light used for irradiating the body portion is less than about 700 nanometers and the emitted light between about 650 and 1100 nanometers. It is preferred that the measurement of decay of the phosphorescence be performed tomographically.

In accordance with another embodiment, the phosphorescent composition is differentially absorbable by the body portion to be imaged. Phosphorescent compositions from the family of chemicals known as porphyrins are preferably employed and said compositions are preferably admixed with proteinaceous compositions which bind with the phosphorescent composition in an amount sufficient to improve the measurement of decay. Albuminous or proteinaceous compositions are preferred.

Certain aspects of this invention have been published in "An Optical Method for Measurement of Dioxygen Concentration Based Upon Quenching of Phosphorescence" Vanderkooi et. al., J. Biol. Chem 262 No. 12, pp 5476–5482 (Apr. 25, 1987) incorporated herein by reference. Two of the co-authors of that paper, Grzegorz Maniara and Thomas J. Green were technicians responsible for carrying out parts of the experiments reported. They were not co-inventors of this invention and were not involved in developing the research program or the described invention.

This invention enables one to obtain three-dimensional images of the vascular system and internal structures of animals using light. The apparatus uses the near infrared phosphorescence emission of dyes to image the distribution of oxygen in the tissue. The dye molecules are excited by light in the visible or near infrared and emit light of wavelengths greater than 650 nm. Long wavelength light in the range of 650–1100 nm is only weakly absorbed by the tissue itself and is little scattered as it passes from the position of the dye to the detector (photographic plate, video camera or other light detector). When a fluorescent molecule is used, the image obtained contains information on the three-dimensional distribution of the dye. When a phosphorescent molecule is used the image obtained contains information on both the dye distribution and oxygen tension. By resolving the lifetime of the phosphorescence, the two components can be separated to obtain three-dimensional image of the interior structure of the tissue as indicated by the varying oxygen concentration therein.

Dye molecules can be injected into the blood stream as either a nontoxic soluble substance or bound to other nontoxic substances. The tissue to be examined is illuminated with a light source of wavelength suitable for excitation of the phosphor and the long wavelength emission collected and optically imaged, preferably onto a video camera. The vascular system can be visualized directly on a video screen or the images can be digitized and enhanced by computer processing. The use of dyes which enter into interstitial spaces or into cells provide different types of information and different views of the tissue.

In carrying out the method of this invention, after injection of the dye molecules, the distribution of oxygen in tissue can be determined. The sample is first pulsed with light and the emitted light produced by the excited phosphors is detected at variable times after the pulse of light. The delay times are selected to optimize determination of the phosphorescence decay curve. The sequence of pulse and time of collection is shown schematically in FIG. 1, wherein $t_d$ is the delay from the beginning of irradiating pulse, 2 to beginning of observation, 4 and $t_g$ is the gate width of the detector. The dotted line indicates the buildup of luminescence signal to maximum $I_o$ and then exponential decay. The time dependence of the intensity of emission light is a function of the oxygen concentration as described in the paper cited above. The time dependence of decay does not depend upon the luminescent probe concentration, thus this method will yield oxygen concentrations independent of the absorption of the exciting light by the tissue and of the concentration of the phosphorescent molecule.

The decay information is preferably collected and evaluated in an imagewise fashion such that a plurality of information carrying pixels are generated. For each pixel in the image, the light intensity as a function of time is evaluated and the oxygen concentration determined. An image which shows the oxygen distribution in the tissue is then constructed.

Figure 2:
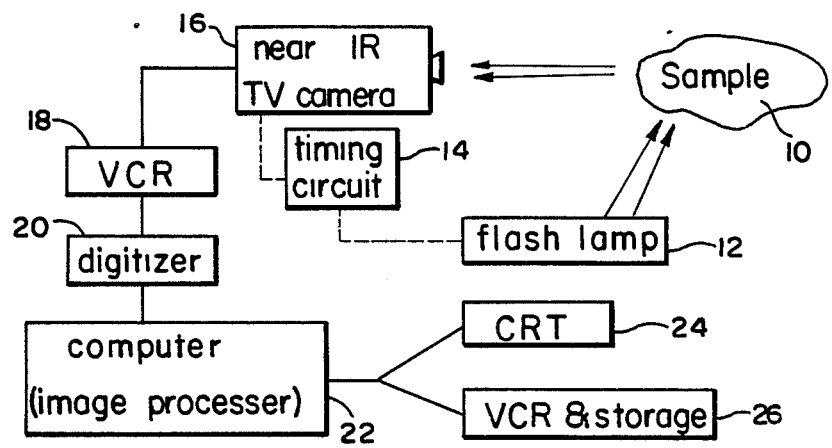
FIG. 2 is a schematic representation of the components of the apparatus of this invention.

An apparatus for carrying out the method of this invention is shown schematically in FIG. 2. All the individual components are well known in the art and are readily available from commercial sources. As shown in FIG. 2, a sample 10 is provided which is a body portion of an animal which has previously been dosed, e.g. injected with a suitable phosphorescent dye chemical compatible with that animal. A light pulse at a wavelength below about 700 nm is provided by a flash lamp 12 which can be a xenon lamp (such as MCP1/FY900 from EG&G Electrooptics Inc., Salem, Mass.) a laser, or another modulated light source. A timing circuit, 14 is provided that triggers lamp 12 and gates a video camera, 16 to detect light only at defined time intervals after the flash. The timing circuit function can be served by a computer. Conventional scanning means for obtaining specially distinct information from a plurality of areas of the body portion is also preferably provided employing combined areas.

The video camera, 16 is on designed to receive light in the near-infrared range. It is timed by timing circuit 14 to receive the light emitted by the phosphorescent dyes in the tissue sample 10 which have been excited by the light from flash lamp 12. Oxygen present in the tissue sample will quench the phosphorescence in relation to the concentration of oxygen. Thus, after a time delay, ($t_d$ in FIG. 1) the emitted light will be less from those portions of the tissue with the greatest concentration of oxygen. The timing of the delay is controlled by timing circuit 14.

The information relating to the emitted light after the delay can be viewed on a cathode ray tube (CRT) or video screen or it can be stored in a video cassette recorder (VCR) 18 and then conveyed to a digitizer 20 to convert analog information into digital form. The information from the digitizer 20 is preferably fed into a computer 22. The analog signal can be digitized such as by using a 20 MHz, 8 bit A/D card (for example, a PCTR-160 card from General Research Corp., McLean, Va. which resides in an AT&T 6300 computer). The computer 22 processes the images in digital form; the images can be suitably and conventionally enhanced The information from computer 22 can be displayed on CRT 24, stored in VCR 26, compared and in general utilized in any concurrent way to generate better knowledge about the oxygen concentration in the body portion scanned. Tomographic representations from the processed information are especially useful. These can be obtained by varying the orientation of the sample relative to the flash lamp and/or the TV camera.

Dye molecules which are suitable to serve as oxygen quenchable phosphorescent compositions include phosphorescent aromatic chemical molecules which emit light in the near infrared. Representative aromatic chemical compounds include porphyrins, fluorescein, erythrosin, phthalocyanins, oxazines, chlorophyll and derivatives of these compounds. Examples of compounds with luminescence which are sensitive to oxygen are verdin, palladium protoporphyrin, and palladium coproporphyrin.

The transport of aromatic molecules into cells varies from cell type depending on whether albumin is the predominant pathway or whether the plasma lipoproteins (VLDL, LDL and HDL) are used. Therefore dyes can be targeted to tissues by choosing dyes which associate either with albumin or the plasma lipoproteins. Such associated dyes differentially absorb into tissue and result in enhanced imaging and in imaging directed at specific tissues. One example of this approach is provided by the work of D. Kessel, P. Thompson, K. Saatio, and K. D. Nantwi, Photochem. Photobiol. 45, 787, 1987, where it was observed that porphyrins with one or two sulfonates bound to the serum lipoproteins and were localized in neoplastic cells, while other porphyrin derivatives bound to albumin and were concentrated in the stromal elements of the tissue. The teachings in that article are incorporated herein by reference. Other means of achieving differential absorption of the dyes can also be used. Cells have very different activities of hydrolytic enzymes such as esterases and peptidases. Phosphorescent molecules with a sufficient number of ionic groups, such as carbolate anion, are thought to be impermeable to cell membranes. When these are selected, derivatized to esters or peptides which are mostly uncharged may be used to facilitate entry into the cells. The probe molecules are then trapped inside only those cells which have high esterase or peptidase activity. Another way to specifically tag particular tissues is to use phosphorescent derivatives of antibodies.

The imaging techniques of this invention are superficially similar in some ways to thermography. In thermography infrared detectors are used to image temperature gradients in human bodies, particular mammary tissue. In thermography the detectors are sensitive to the longer wavelength infrared emission due to tissue heat; the image must be constructed from very weak light in which the difference in emission intensity from one region of the tissue to another is at most a few percent. With the systems of this invention the light emission intensities will differ by many fold and the emission intensity will have sharp gradients (over a few microns), whereas thermal gradients are small (over a few millimeters). Thus, good imaging is expected.

This invention will now be described in connection with the following non-limiting example thereof.

The method and apparatus of this invention can be useful in examining soft tissue for anomalies in the vasculature which generally accompany tumor formation and for obtaining detailed diagnostic information on all types of vascular defects (e.g., constrictions, varicosities, aneurisms, etc.). Vascular surgery can be greatly aided by thorough visual examination of the vessels prior to operating. Wound vascularization and tissue oxygenation are diagnostic of the healing process and a knowledge of the growth of new vessels into the affected are and its extent of oxygenation would be very important in treatment.

The technique can also be used to image tumors directly as it is well known that some tumors will concentrate prophyrins or other dyes. Some tumors naturally contain porphyrins, in this case, visualization will be possible without dye injection. Another application would be to visualize cysticerci of some parasites, such as *Taenia solium*, which also naturally contain porphyrins. Again, their visualization would greatly aid in diagnosis and treatment of disease.

The invention will be a powerful diagnostic tool when used to determine the three-dimensional oxygen distribution. In the vascular system the presence of abnormal oxygen pressure is diagnostic of the severity o circulatory deficiencies and wound healing is critically dependent on oxygen pressure in the wound area. Radiation treatment of tumors requires oxygen for maximal effectiveness so knowledge of the oxygen distribution and possible anoxic spots would be invaluable in determining the treatment of choice.

EXAMPLE

C57BL/6 female mice bearing pancreatic tumor Panc 02 implanted subcutaneously are used for this example. Animals are treated with 10 mg/kg of the zinc verdin, bound to albumin, as the dye chemical, which is given by intravenous injection 4 hours before the experiment is carried out. Zn verdin is a derivative of porphyrin which absorbs at 600 nm and is available from Porphyrin Products (Logan, UT). Monochromatic light at below about 700 nm from an light emitting diode laser (1 watt) is used for excitation; the light is pulsed with pulse duration of about 1 microsecond and directed at the location of the tumor. The light emitted from the dye chemical within the tumor above 800 nm is collected by using a optical cut-off filter. A video camera records a spatial distribution or image of the intensity of the emitted light. The starting time for the collection of data occurs at variable delay after the lamp flash. The times vary from a few microseconds to milliseconds. For each time picture of light intensity is obtained. From calculation of light intensity as a function of time at each pixel the distribution of oxygen concentration in the tumor and surrounding tissue and, thus, a determination of its structure, is obtained.

The three-dimensional distribution of the oxygen concentration in the animal can be obtained using conventional tomographic techniques. The angle of the exciting light or the angle of the collection of the emitting light is changed. By the change of the light intensity due to different depth of penetration, three-dimensional images of the interior body part can be obtained.

We claim:

1. A method for imaging oxygen-containing internal body portion of a host animal which comprises:
   (a) adding and mixing into a body fluid of the host animal a phosphorescent composition compatible with said body fluid, the phosphorescence of said composition being quenchable with oxygen in said body portion;
   (b) irradiating said body portion with a pulse of light of a wavelength and for a time sufficient to effect phosphorescence of said composition to be omitted as light from said body portion, which phosphorescence decays with time;

(c) scanning across said body portion to detect said emitted light and the decay of said emitted phosphorescence across said body portion;

(d) relating any variations in said decay across said body portion to variations in structure of said body portion based on oxygen contained by the body portion; and (e) displaying an image of said variations in structure of said body portion based on oxygen contained by said body portion.

2. The method of claim 1 wherein said wavelength is about below 700 nanometers.

3. The method of claim 2 wherein said emitted light wavelength is between about 650 and 1100 nanometers.

4. The method of claim 1 wherein said measurement of the decay is accomplished by measuring the intensity of the emitted phosphorescence at a plurality of times after the irradiation and determining the time dependence of said decay.

5. The method of claim 1 wherein said step of displaying an image is performed tomographically with respect to said body portion.

6. The method of claim 1 wherein said phosphorescent composition is differentially absorbable by said body portion.

7. The method of claim 1 wherein said body portion is a vascular body portion.

8. The method of claim 7 wherein said body portion is soft tissue with vascular anomalies.

9. The method of claim 7 wherein said body portion is an area of infarction.

10. The method of claim 7 wherein said body portion is an area of altered vascularization.

11. The method of claim 1 wherein said phosphorescent composition is a phosphorescent porphyrin.

12. The method of claim 1 wherein the phosphorescent composition is selected from the group consisting of zinc verdin, palladium coproporphyrin and palladium protoporphyrin.

13. The method of claim 1 wherein said phosphorescent composition is admixed with a proteinaceous composition bindable therewith in an amount sufficient to improve the measurement of decay.

14. The method of claim 13 wherein said proteinaceous composition is albuminous.

15. A method for imaging oxygen-containing, internal body portions of a mammal which comprises:

(a) adding and mixing into the circulatory system of said mammal a phosphorescent composition compatible with said system, the phosphorescence of said composition being quenchable with oxygen, said composition being differentially absorbable by said body portion;

(b) irradiating said body portion with a pulse of light at a wavelength less than about 700 nanometers for a time sufficient to effect phosphorescence of said composition to be emitted as light of a wavelength above about 650 nanometers from said body portion, which phosphorescence decays in intensity with time;

(c) scanning across said body portion to detect and record the intensity of the emitted phosphorescence at a plurality of times after said irradiating step;

(d) determining the time dependence of decay of said intensity across said body portion;

(e) relating any variations in said decay across said body portion based on contained oxygen, absorbed phosphorescent composition or a combination of contained oxygen and absorbed phosphorescent composition; and (f) displaying an image of said body portion based on said variations in decay of step (e).

16. The method of claim 15 wherein said relating step (e) includes the digitizing of said time dependence of decay determined in step (d) to provide for three-dimensional imaging of said body portion.

17. An apparatus for imaging an oxygen-containing internal body portion of a host animal, which body portion contains body fluid in which a phosporescent composition quenchable with oxygen is mixed, which apparatus comprises:

(a) means for irradiating said body portion with a pulse of light at a wavelength less than about 700 nanometers for a period of time sufficient to effect phosphorescence in said phosphorescent composition, the intensity of which decays with time;

(b) means for scanning across said body portion to detect the intensity of the phosphorescent emitted light from said composition at a wavelength greater than about 650 nanometers;

(c) timing means for regulating said irradiating means and said scanning means to scan said emitted light at different locations across said body portion only at determined time intervals after said irradiating pulse;

(d) means to measure decay in said intensity of said emitted light at each location across said body portion at said determined time intervals;

(e) means to relate any variations in said decay at said locations across said body portion to the structure thereof; and (f) means for displaying an image of said body portion based on relation of said variations in decay at said locations across said body portion to the structure thereof.

18. The apparatus described in claim 17 including means to digitize the variations in said decay at said locations across said body portion.

* * * * *

UNITED STATES PATENT AND TRADEMARK OFFICE
CERTIFICATE OF CORRECTION

PATENT NO. : 4,947,850

DATED : August 14, 1990

INVENTOR(S) : Jane Vanderkooi and David Wilson

It is certified that error appears in the above-identified patent and that said Letters Patent is hereby corrected as shown below:

Col. 3, line 49, insert --a-- before three-dimensional;
Col. 4, line 43, delete the word "on" and insert therefor --one--;
Col. 6, line 4, delete the word "are" and insert therefor --area--;
Col. 6, line 18, delete "o" and insert therefor --of--;
Col. 6, line 68, delete "omitted" and insert therefor --emitted--.

Signed and Sealed this

Nineteenth Day of November, 1991

Attest:

HARRY F. MANBECK, JR.

*Attesting Officer*  *Commissioner of Patents and Trademarks*